United States Patent [19]
Hovey

[11] 4,043,637
[45] Aug. 23, 1977

[54] PHOTOCHROMIC LIGHT VALVE
[75] Inventor: Richard J. Hovey, Sturbridge, Mass.
[73] Assignee: American Optical Corporation, Southbridge, Mass.
[21] Appl. No.: 619,749
[22] Filed: Oct. 6, 1975

Related U.S. Application Data

[63] Continuation-in-part of Ser. No. 370,247, June 15, 1973, abandoned, which is a continuation-in-part of Ser. No. 268,317, July 3, 1972, abandoned.

[51] Int. Cl.² ............................................. G02F 1/17
[52] U.S. Cl. ................................................ 350/160 P
[58] Field of Search .................... 350/160 P; 252/300

[56] References Cited
U.S. PATENT DOCUMENTS

| | | | |
|---|---|---|---|
| 3,475,339 | 10/1969 | Foster et al. | 350/160 P |
| 3,485,764 | 12/1969 | Kazan | 350/160 P |
| 3,508,810 | 4/1970 | Baltzer | 350/160 P |
| 3,540,793 | 11/1970 | Araujo et al. | 350/160 P |
| 3,666,352 | 5/1972 | Wagner et al. | 350/160 P |

OTHER PUBLICATIONS

Meriwether et al. "The Photochromism of Metal Dithizonates," J. Am. Chem. Soc., vol. 87 (Oct. 20, 1965) pp. 4441–4448.

Primary Examiner—William L. Sikes
Attorney, Agent, or Firm—H. R. Berkenstock, Jr.; William C. Nealon

[57] ABSTRACT

A lens having an optical density which is variable under differing light conditions can be produced by imbibing a synthetic polymer lens such as a polycarbonate or diethylene diglycol bis allyl carbonate polymer with a solution of a metal dithizonate. A polarizing sheet can be laminated thereto or alternatively, a passive dye can be utilized on the inner surface of the lens to provide non-variable reduced optical density in the assembly.

19 Claims, 8 Drawing Figures

PHOTOCHROMIC LIGHT VALVE

CROSS-REFERENCE TO RELATED APPLICATION

This application is a continuation-in-part of copending application Ser. No. 370,247 filed June 15, 1973 and now abandoned which is a continuation-in-part of Ser. No. 268,317 filed July 3, 1972 and now abandoned.

BACKGROUND OF THE INVENTION

This invention is related to ski goggles or the like and is more particularly concerned with an improved construction which is useful under differing ambient light conditions.

Skiing has become recently a major winter sports activity for increasing numbers of people of all ages. Ski goggles perform a dual function for the skier. Firstly, the ski goggles provide a shield in front of the eyes to protect the eyes from the wind and thereby prevent tearing. Tearing obstructs vision and is dangerous to the skier. Secondly, the ski goggle is fitted, in most instances, with a lens formed of a material which is absorbent to light.

The greatest quantity of ski goggles sold at the present time are provided with two sheets of colored filter material which may be switched manually by the skier to provide accommodation for different ambient light conditions which occur during various portions of the day. Usually, a dark colored filter is placed in the goggle frame for bright sunshine during the middle part of the day. The dark colored filter used for bright sunlight is usually a neutral grey or green color and has a visual transmittance on the order of 10% to 20%. Normally, a yellow filter is used in the diffuse light which occurs in the later part of the afternoon or in shaded areas. For this more diffuse lighting, the yellow filter is used to permit better visibility of surface variations of the ski slope.

Ski goggles have been proposed in the past with a photochromic composition included in the lens. These ski goggle lenses are intended to change color under the influence of sunlight, particularly the ultraviolet wavelengths of light.

Photochromic compounds change color on exposure to and/or withdrawal from specific types of electromagnetic radiation. The known compounds that are reversible, i.e., change from one color to another under the influence of certain electromagnetic radiation and change back to the original color in the absence of that electromagnetic radiation have found use in very few practical applications. Usually, the electromagnetic radiation is light in the ultraviolet portion of the electromagnetic spectrum. The impracticality is largely due to the limited useful life of the compounds. To be satisfactory in ski goggles, these compounds must react quite rapidly to the activating radiation and they must have a reasonable useful life.

It is known that, in general, a photochromic reaction is produced by a photochromic substance which contains bi-stable atoms and/or molecules which are capable of changing back and forth between two distinct energy states. Generally, the changes between the different states are induced by absorbed radiant energy and the differences of state may be different atomic, molecular, or electronic configurations.

The few ski goggles available having a photochromic composition included therein, however, have been poorly accepted as the useful life of these goggles is extremely limited. In one case, goggles have been proposed using a liquid solution of the photochromic composition, which is, of course, not at all satisfactory in an active sport such as skiing and particularly in very cold weather. Other ski goggles previously available have had a very limited life, and generally a very slow response for the photochromic reaction. As the goggles aged, the reaction time becomes longer and longer.

The production of satisfactory photochromic filters for ski goggles and other purposes has been a continuing problem, mainly because of the very limited useful life of the chemicals involved in the photochromic reactions. A few inorganic compounds are known to be fairly resistant to breakdown upon continual color change reactions; however, such compounds react too slowly to provide satisfactory photochromic ski goggle filters. Some metallo-organic compounds have been satisfactory with respect to the time of return factor; however, the incorporation of these materials in the filter support has presented many problems. Most of such compounds perform their reactions quite well in solutions, but when incorporated in a solid their effectiveness is reduced appreciably. Furthermore, to be a potentially useful photochromic compound for use in ski goggles, the absorption characteristics of the two energy states must closely match the requirements of the application, i.e. the absorption characteristics must be quite different and in particular portions of the electromagnetic spectrum.

SUMMARY OF THE INVENTION

Accordingly, it is an object of the present invention to provide an improved construction for a photochromic light valve lens useful as a ski goggle wherein variable optical density eye protection is provided without requiring multiple lenses.

Another object of the invention is to provide a method for producing a photochromic light valve lens.

Another object of the invention is to provide an improved ski goggle and method for its production wherein the photochromic lens reacts quickly to the activating radiation and recovers quickly following the removal of that radiation, even at cold temperatures.

A further object of the invention is to provide such an improved ski goggle and method wherein the photochromic material is present in a durable form.

A still further object of the invention is to provide such an improved ski goggle and method wherein protection is afforded to the material from ultraviolet radiation.

Briefly, the invention in its broadest aspect encompasses a light valve substrate comprising at least one synthetic plastic substrate imbibed with an effective quantity of a metal dithizonate. The metal dithizonate is imbibed in at least one polymer substrate by immersing the substrate in a heated saturated solution of the metal dithizonate in a solvent for an extended period of time. This provides a substrate suited for use in a ski goggle which in its inactive state allows a luminous transmission of no more than approximately 50% of the light and maintains a characteristic yellow coloration and which, when activated by visible light, attains a grey coloration having a reduced luminous transmittance, preferably attaining a luminous transmission of approximately 10%.

The combination of either a passive dye or a polarizing layer together with a metal dithizonate contained in a polymeric substrate to obtain a light valve effect provides a means of overcoming the effects of saturation of a metal dithizonate layer. Saturation occurs upon exposure of the metal dithizonate to visible light in order to activate it. As is well known, saturation activation of a metal dithizonate can result in shifting the absorption characteristics from the yellow end of the visible spectrum to the red end. When this occurs, the net effect on luminous transmittance can be little or no change since the decreased yellow absorption of the metal dithizonate upon saturation may not be balanced by the increased red absorption.

According to the invention, a light valve effect can be obtained by incorporating into the polymer a passive dye which absorbs in the yellow area of the visible spectrum so that upon saturation activation of the metal dithizonate there is obtained a net decrease in luminous transmission. Alternatively, a standard polarizing layer can be laminated to a polymer substrate containing the metal dithizonate to obtain the desired light valve effect. In this embodiment of the invention, reduced luminous transmission is obtained both in the unactivated and activated state resulting from the polarizing effect. The effect of saturation activation can be avoided by the passive dye absorption effect as described above. In this embodiment, the iodine dye utilized to form the polarizing sheet functions as the passive dye.

Suitable passive dyes include but are not limited to anthraquinone dyes such as quinizarin, Color Index (C.I.) number 58050, and anthraflavone, C.I. 58950; natural organic dyes such as chrysophanic acid, C.I. 75400 and rhamnetin, C.I. 75690; disazo dyes such as pigmet yellow, C.I. 21090, and solvent yellow, C.I. 21240; and monoazo dyes such as solvent yellow, C.I. 11020, and pigment yellow, C.I. 11680.

The solvent or mixture of solvents utilized in the treating solution are not among those that can be considered true solvents for the synthetic polymer lens which is to be treated. This is so that the optical clarity of the lens will be unaffected by immersion in the heated saturated solution of the metal dithizonate.

For the treatment of a lens consisting of a polymer of diethylene glycol bis allyl carbonate, it is desirable to immerse the lens in a solution of a metal dithizonate in a solvent selected from an aromatic hydrocarbon and mixtures of an aromatic hydrocarbon and a solvent individually selected from glycerol, a glycol having 2 to about 8 carbon atoms and an alcohol having 2 to about 10 carbon atoms or mixtures thereof. Suitable aromatic hydrocarbon solvents include but are not limited to benzene, toluene, xylene, ethylbenzene, $n$-propylbenzene, $n$-butylbenzene, $t$-butylbenzene, 1,3,5-triethylbenzene, styrene, allylbenzene, mesitylene and prehnitene.

For the treatment of a lens of Bisphenol-A polycarbonate to render it photochromic, it is desirable to immerse the lens in a solvent individually selected from glycerol, a glycol containing 2 to 8 carbon atoms, an alcohol having 2 to 10 carbon atoms or mixtures thereof containing the metal dithizonate. Suitable glycol solvents include but are not limited to ethylene glycol, propylene glycol, 1,3-butylene glycol, 2,3-butylene glycol, 1,4-cyclohexylene dimethanol, 2,3-hexanediol, 2-ethyl-1, 3-hexanediol, neopentyl glycol, glycerol, mono-methyl ether of glycerol and mono-ethyl ether of glycerol. Suitable alcohol solvents include but are not limited to ethanol, propanol, butanol, n-hexyl alcohol and cyclohexanol.

The temperatures of the treating solution used in the imbibing process of the invention can be any suitable temperature so chosen that the imbibition reaction proceeds with the desired speed and the optical clarity of the synthetic polymer lens is not adversely affected by the solvent of the treating solution. Preferably, a temperature of about 25° C to about 150° C is utilized, said temperature also being chosen so that the boiling point of the solvent medium of the treating solution is not exceeded. Generally, the depth of penetration of the photochromic material in the polymer lens is up to 20 microns. Preferably, penetration to a depth of about 1 to about 10 microns is obtained.

The polymer substrate of the invention containing the photochromic material can be laminated with a standard polarizing sheet or a passive dye, that is, one that does not change color upon exposure to light can be incorporated into the polymer substrate either by imbibition or by application to the substrate as a coating. Preferably, the passive dye is present on the inner or back side of the substrate (side away from the side of the substrate normally exposed to light) in order to avoid reducing any of the apparent light sensitivity of the metal dithizonate. By use of a passive dye and/or a polarizing layer together with a metal dithizonate, a substantial reduction in luminous transmission, as compared to the unactivated form of the substrate, can be obtained.

A polymer substrate imbibed with only a metal dithizonate prepared according to the process of the invention exhibits in the unactivated state a luminous transmission of about 40% to about 50%, preferably at least about 45% to about 50%. Upon activation by visible light, a luminous transmission of about 5% to about 45% can be obtained, preferably about 15% to about 25%.

With the same metal dithizonate-imbibed substrate laminated to a standard polarizing sheet, the unactivated luminous transmission is substantially reduced to about 15% to about 20%.

The same metal dithizonate-imbibed substrate to which a passive dye is applied to the back side or side away from the side normally exposed to visible light provides a minimum reduction in unactivated luminous transmission but a substantially reduced luminous transmission upon activation by visible light. Thus, using a 5 micron coating of quinizarin (a passive dye) applied to the back side of the substrate from a toluene solution of the dye and polymethylmethacrylate, activated luminous transmission of about 15% to about 25% is attained. In another modification, a standard polarizing sheet is imbibed with a metal dithizonate and this may then be used alone or overlaid on a hard optical quality plastic substrate. In the latter case, an ultraviolet absorbing agent may be incorporated in the plastic substrate to increase the fatigue resistance of the photochromic ski goggle lens to the ultraviolet radiation. In another modification, a soft, synthetic plastic may be imbibed with a metal diethizonate overlaid on a sheet of hard optical quality plastic and the standard polarizing sheet overlaid over the soft plastic to form a laminated lens.

Further objects, advantages, and features of the invention will be apparent in the arrangement and construction of the constituent parts, in detail, as set forth in the following specification taken together with the accompanying drawing.

DETAILED DESCRIPTION OF THE PREFERRED EMBODIMENTS

Figure 1:
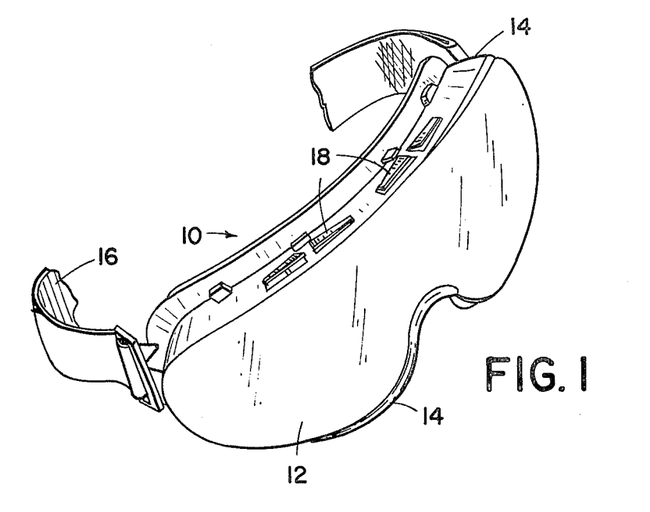
FIG. 1 is a perspective view of one form of an improved ski goggle according to the present invention showing the general configuration thereof.

Referring initially to FIG. 1, there is shown an improved ski goggle indicated generally by numeral 10. The ski goggle 10 includes a lens element 12 fixedly fitted into a frame 14. The frame 14 is essentially a face fitting frame enclosing the eye area of the wearer's face. The frame 14 includes vents 18 for allowing air to circulate within the goggle. It is formed of a resilient material so as to conform comfortably to the face of the wearer. An elastic band 16 provides means for holding the ski goggle frame in position on the user. This figure illustrates one common form of ski goggle having a continuous lens from side to side in a generally hour-glass shape extending over the bridge of the nose. This configuration is the most popular at present as the peripheral vision of the wearer is only minimally impeded. As will be seen from the following description, the lens of the present invention is not to be limited to this configuration, but rather, is useful in any chosen ski goggle configuration.

Figure 2:
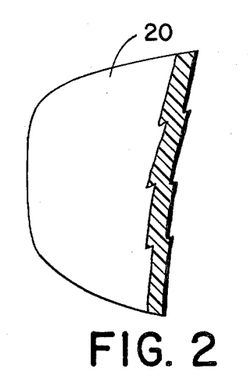
FIG. 2 is an enlarged detail view of a ski goggle lens arranged for mounting in the frame of the goggle of FIG. 1, showing, in cutaway section, details of a feature of the present invention.

FIG. 2 shows a portion of the lens element 12 from the improved ski goggle of FIG. 1. This lens is formed of a single layer of plastic material which is imbibed with a photochromic compound according to the invention.

The invention involves a filter or lens useful for the ski goggles of FIG. 1, wherein the filter includes at least one synthetic plastic member imbibed with a photochromic composition, specifically a metal dithizonate. The general formula for the metal dithizonate is as follows:

wherein M is $Hg^{II}$, $In^{III}$, or $Ga^{III}$, when M is $Hg^{II}$, $x$ is 1 or 2 and $y$ is 2-x, and when M is $In^{III}$ or $Ga^{III}$, $x$ is three and $y$ is zero, R and R' are, individually

$R^2$ is an alkyl ($C_1$–$C_4$), a nitro, a halo, an alkoxy ($C_1$–$C_4$), an aryloxy ($C_6$–$C_{10}$), a hydroxy, a carboxy, a carboxyalkyl ($C_2$–$C_4$), an alkoxycarbonyl ($C_2$–$C_6$), an arylamino ($C_6$–$C_{10}$), an acylamino ($C_1$–$C_{11}$), or an alkylthio ($C_1$–$C_4$) radical, and R" is selected from an alkyl ($C_1$–$C_{12}$) such as methyl, ethyl, propyl, butyl, secondary butyl, tertiary butyl, hexyl, octyl, 2 ethyl hexyl, and dodecyl, an aryl ($C_6$–$C_{18}$) such as phenyl and naphthyl, an alkaryl ($C_7$–$C_{10}$) such as tolyl and xylyl, an aralkyl ($C_7$–$C_{15}$) such as benzyl, an alkoxyalkyl ($C_2$–$C_{12}$) such as ethoxyethyl and propoxyoctyl, and an aminoaryl ($C_6$–$C_{12}$) such p-aminophenyl.

More particularly, compounds having the following formula have been found to be especially useful in the present invention:

wherein Ph is a phenyl ring, M is $Hg^{II}$, $In^{III}$, or $Ga^{III}$, when M is $Hg^{II}$, $x$ is 1 or 2 and $y$ is 2-x, when M is $In^{III}$ or $Ga^{III}$, $x$ is three and $y$ is zero, and R" is selected from phenyl, naphthyl, tolyl, ethyl, ethoxyethyl, benzyl, and p-aminophenyl.

Specifically, the following photochromic metal dithizonates have been incorporated in a variety of plastic substrates according to the invention: 1. bis (diphenylthiocarbazono) mercury (II)

2. (diphenylthiocarbazone) phenyl mercury (II)

3. (diphenylthiocarbazono) β-naphthyl mercury (II)

4. (diphenylthiocarbazono) p-tolyl mercury (II)

5. (diphenylthiocarbazono) ethyl mercury (II)

6. (diphenylthiocarbazono) ethoxyethyl mercury (II)

7. (diphenylthiocarbazono) benzyl mercury (II)

8. (diphenylthiocarbazono) p-aminophenyl mercury (II)

9. tris (diphenylthiocarbazono) indium (III)

10. tris (diphenylthiocarbazono) gallium (III)

In general, the foregoing metal dithizonates are synthesized by interacting stoichiometric quantities of dithizone (see U.S. Pat. No. 3,519,635) and a metal salt. The metal salt is first dissolved in ethanol. This solution is then added to a chloroform solution of dithizone. The reaction solution is refluxed for approximately two hours during which time the metal dithizonate separates from the reaction solution. The product is then separated by suction filtration, is air dried, and recrystallized from chloroform.

Various types of synthetic plastic substrates can be imbibed with sufficient metal dithizonate to form an improved lens utilizing polymer and copolymers thereof including: (1) allyl polymers such as CR-39 (diethylene glycol bis allyl carbonate); (2) polycarbonate; (3) poly-lower aliphatic methacrylates, such as polymethylmethacrylate, polyethyl methacrylate, polyisobutyl methacrylate, and poly-n-butyl methacrylate; (4) cellulosic polymers, such as cellulose acetate, cellulose acetate butyrate, and cellulose caprate; (5) vinyl polymers such as polyvinyl alcohol, polyvinyl butyral, and polyvinyl acetate; (6) hydroxylated polyethylene, and like plastics which are available as optically clear compositions and which may be molded, injected, poured, drawn, cast or otherwise formed into lenses. In addition, standard polarizing sheet material previously dyed with iodine can be imbibed with a metal dithizonate to form improved ski goggles having polarizing characteristics as well as photochromic properties.

Generally, a synthetic plastic lens is formed initially and then is imbibed with the metal dithizonate by immersing the synthetic plastic substrate in a solution of the metal dithizonate in one of the above solvents for extended periods of time and preferably at elevated temperatures. In a preferred mode of imbibing the synthetic plastic substrate with the metal dithizonate, it is maintained in a boiling solution of the photochromic compound for at least about 24 hours. This permits an effective quantity of the photochromic compound to be imbibed in the substrate to form an effective ski goggle lens.

The following specific examples show various methods of forming a synthetic plastic substrate imbibed with a photochromic composition.

EXAMPLE 1

In a preferred embodiment, a ski goggle lens formed of optically clear CR-39 substrate is imbibed with a photochromic compound by immersion of the lens in a boiling saturated toluene solution of the photochromic composition. A saturated solution of bis (diphenylthiocarbazono) mercury (II) in toluene is brought to a boil. The lens is immersed in the solution and is retained in the boiling solution for at least 24 hours. The solution may be refluxed effectively to maintain the solution, during the immersion. After removal from the toluene solution, the lens is rinsed immediately with toluene or methanol and wiped dry.

Figure 3:
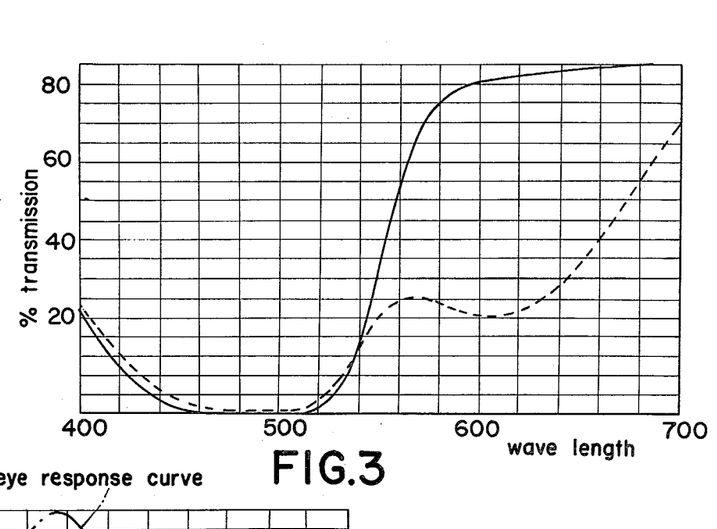
FIG. 3 is a graph showing the transmission spectra both before and after activation of a ski goggle lens according to FIG. 2 treated with a photochromic composition.

The resultant ski goggle lens was examined for electromagnetic radiation absorption, both before and after activation. The resulting curves are shown in FIG. 3. In the 500 to 700 nm wavelength range, the activated lens absorbs the radiation to a marked degree. A CR-39 lens treated in the manner described has a yellow to orange color in the unactivated state, and when activated by visible light in the 400–555 nm wavelength range changes to a grey or bluish-grey color. The filter material in its unactivated state allows approximately 45% transmission of light. On being activated by visible light it has a visual transmittance of approximately 10%. Therefore, it may be seen that not only is there a shift in coloration as is desirable in a ski goggle from yellow to grey, but there is also a marked decrease in the visual transmittance of the lens as is a prime requisite of such a photochromic ski goggle lens.

Figure 4:
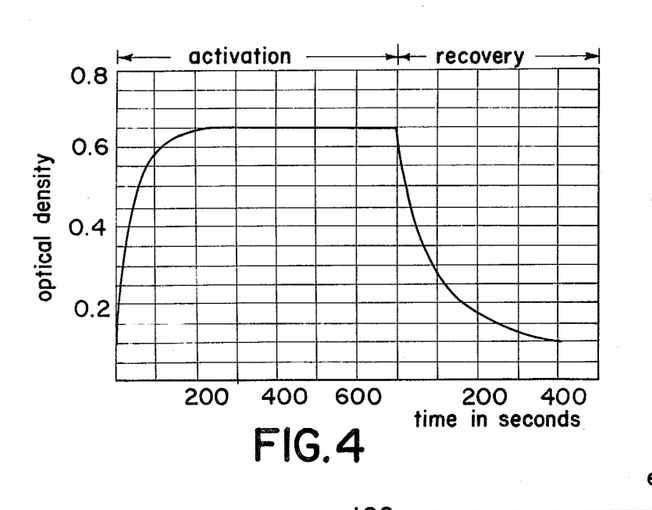
FIG. 4 is a graph showing the reaction rates of activation and recovery of the lens of FIG. 3.

The graph of FIG. 4 depicts the change in optical density versus time for a ski goggle lens according to Example 1 throughout a complete activation and recovery cycle. The monitoring wavelength is 620 nm. It can be seen that the lens becomes fully activated within three minutes, but more importantly, the lens is over 80% activated within the first minute of exposure. Therefore, a wearer entering into an area of bright sunlight from shade perceives an immediate and significant change in density and coloration.

Similarly, FIG. 4 depicts the response of the lens to removal of the activating electromagnetic radiation. The recovery is not as fast as the activation rate; however, this is characteristic of photochromic materials. However, the lens has recovered by approximately 50% within the first minute following removal of the activating radiation.

Furthermore, it should be noted that the activating radiation is in the visible region of the electromagnetic spectrum as compared to the ultraviolet for most photochromic compounds. This fact allows for greater effectiveness of the ski goggles since the activating radiation is more generally present when protection is desired.

In a ski goggle application, one of the main requirements is a change in spectral characteristics, i.e. from a grey color for use in bright sunlight to a yellow (blue absorption) color for use in the diffuse light which occurs in the later part of the afternoon or in areas of shade.

EXAMPLE 2

Figure 5:
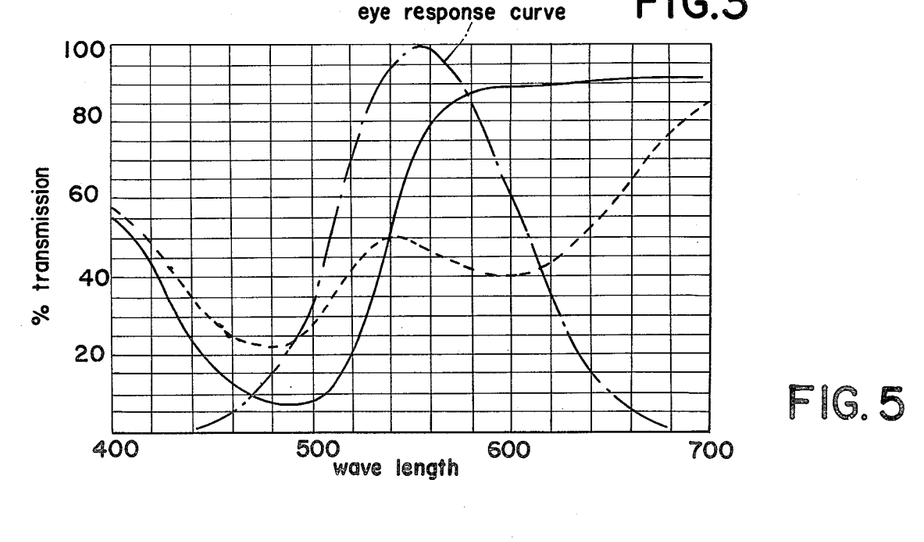
FIG. 5 is a graph showing the transmission spectra both before and after activation of another ski goggle lens according to FIG. 2 having a modified photochromic chemical imbibed on the lens.

A ski goggle lens made of CR-39 is immersed in a boiling saturated solution of (diphenylthiocarbazono) phenylmercury (II) in toluene for a period of about 24 hours. At the end of this period, the substrate is removed and immediately rinsed with toluene or methanol and wiped dry. The lens is subjected then to an absorption test, the results of which are shown in FIG. 5. This graph shows the absorption of the lens both before and after activation of the photochromic material.

The visual or luminous transmission may be changed by an alteration in the position of an absorption band even though the intensity of the transmitted light integrated over the visible region of 400–700 nm wavelength remains unchanged. The total area under the transmission curve in FIG. 5 (obtained from a spectrophotometer) is only about 20% higher in the unactivated state than in the activated state. The visual transmission of the ski goggle lens is about 50% in the unactivated state (yellow) and about 15% in the activated (grey) state. This is due to the fact that the human eye responds most strongly to a very narrow band of wavelengths centered at about 550 nm in the middle of the visible region, as illustrated by the eye response curve which is also plotted in FIG. 5. This illustrates that when such a narrow, intense absorption band falls near the center of the eye response curve it will decrease the visual transmittance a great deal, whereas an absorption band of similar shape and intensity but located on either edge of the eye response curve would decrease the visual transmittance only slightly.

Thus far, the invention has been described in terms of an economical process by which an effective variable density ski goggle lens is formed. By increasing the complexity of the process only a minimal amount, numerous other beneficial effects may be attained with the present invention. The following examples provide an indication of the possibilities for use of the instant invention.

EXAMPLE 3

A ski goggle lens formed of optically clear substrate of diethylene glycol bis allyl carbonate sold under the trademark "CR-39" is imbibed with a photochromic compound by immersion of the lens in a boiling saturated solution in toluene of the photochromic composition. A saturated solution of bis (diphenylthiocarbazono) mercury (II) in toluene is brought to a boil. The lens is immersed in the solution and is retained in the boiling solution for at least 24 hours. The solution may be refluxed effectively to maintain the solution during the immersion. After removal from the toluene solution, the lens is rinsed immediately with toluene or methanol, wiped dry and bonded to a polarizing sheet (i.e. a polyvinyl alcohol film unidirectionally stretched prior to dyeing with iodine).

The resultant ski goggle lens was examined for electromagnetic radiation absorption, both before and after activation. In the 500 to 700 nm wavelength range, the activated lens absorbs the radiation to a marked degree. A CR-39 lens treated in the manner described has a yellow to orange color in the unactivated state, and when activated by visible light in the 400-555 nm wavelength range changes to a grey or bluish-grey color. The filter material in its unactivated state allows approximately 25% transmission of light. On being activated by visible light it has a visual transmittance of approximately 10%. Therefore, it may be seen that not only is there a shift in coloration as is desirable in a ski goggle from yellowish grey to dark grey, but there is also a marked light valve effect, i.e. a decrease in the visual transmittance of the lens which is a prime requisite of such a photochromic ski goggle lens.

EXAMPLE 4

A ski goggle lens made of CR-39 is immersed in a boiling toluene solution of (diphenylthiocarbazono) phenylmercury (II) for a period of about 24 hours. At the end of this period, the substrate is removed and immediately rinsed with toluene or methanol, wiped dry and bonded to a polarizing sheet.

EXAMPLE 5

Figure 6:
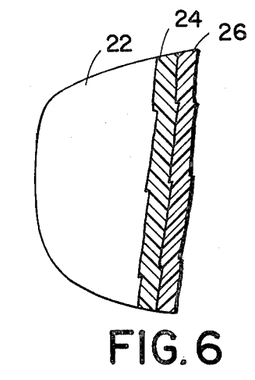
FIG. 6 is a detail view of a lens for a ski goggle illustrating in cutaway section the laminated construction with a hard optical substrate imbibed with a metal dithizonate and a polarizing sheet.

A modified ski goggle lens is shown in FIG. 6 and is a composite or laminated lens 22. In this case, the lens 22 is formed of a layer 24 of cellulose acetate butyrate which is bonded to a sheet of polyvinyl alcohol 26 (or polyvinyl butyral) which was unidirectionally stretched prior to bonding to the cellulose acetate butyrate sheet, and subsequently dyed with an iodine composition dye. This is a well-known technique for producing a polarizing material. This lens after lamination is imbibed with a metal dithizonate. The resulting lens provides approximately 29% luminous transmittance, in the unactivated state and again approximately 10% luminous transmission in the activated state making the lens suitable as a light valve.

EXAMPLE 6

Another form of the ski goggle lens of Example 5 is achieved by imbibing the substrate with the metal dithizonate prior to bonding of the polarizing sheet to the substrate to form the composite ski goggle lens.

EXAMPLE 7

A ski goggle lens also may be made by imbibing the photochromic material into a relatively soft matrix and then securing the soft matrix to a relatively hard substrate. It is a characteristic of photochromic materials that photocoloration efficiency is enhanced appreciably in going from a relatively hard matrix (high glass transition temperature polymer) to a relatively soft matrix (low glass transition temperature polymer). Further, the glass transition temperature of a given polymer may be further lowered through incorporation of a plasticizer, for example, dibutyl phthalate, into the plastic matrix. By using a laminate, a very soft plastic may be incorporated into a ski goggle lens, to produce a very effective photochromic ski goggle. Such a ski goggle lens exhibits faster activation and recovery rates than even these illustrated in FIG. 4. However, due to the soft nature of the imbibed matrix, a third layer should be incorporated into the laminate to cover and protect the soft matrix from scratching.

Figure 7:
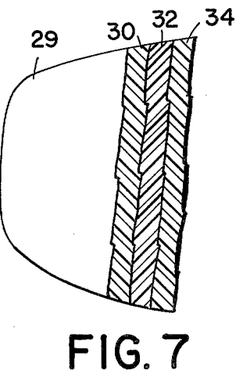
FIG. 7 is a detail view of a portion of a lens for a ski goggle illustrating a laminated structure with a soft, synthetic plastic imbibed with a metal dithizonate.

Such a plastic lens or plastic substrate 20, preferably formed of CR-39, is overlaid with a sheet 22 formed of soft, plastic material imbibed with one of the photochromic materials specified above. The sheet 22 may be a plastic sheet plasticized with a plasticizer, for example, dibutyl phthalate in a cellulose acetate butyrate, and this material is bonded to the substrate 20. A standard polarizing sheet 24 may be bonded over the photochromic composition containing sheet 22 to complete the lens. As pointed out above, the standard material may be a laminate formed of a layer of cellulose acetate butyrate bonded to a sheet of polyvinyl alcohol which has been unidirectionally stretched and dyed with an iodine dye prior to bonding to the cellulose acetate butyrate sheet. Two layers of this laminate can then be bonded over the soft plastic material 22 to form a ski goggle lens.

EXAMPLE 8

Figure 8:
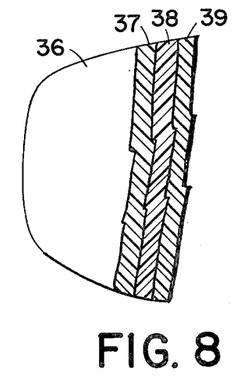
FIG. 8 is a detail view of a portion of a ski goggle lens showing a modified laminated structure.

In a modification of a method of Example 6, a laminated ski goggle lens is formed in a similar manner; however, an ultraviolet absorbing agent is incorporated into the lens substrate to increase the fatigue resistance of the photochromic material, thus greatly improving the useful life thereof. As shown in FIG. 8, a lens 36 comprises a layer 37 formed preferably of CR-39 (allyl diglycol carbonate) material having an ultraviolet absorbing agent incorporated therein. A soft plastic sheet 38 which is imbibed with a photochromic dithizonate is bonded to the layer 37. The unit is completed by bonding a standard polarizing sheet 39 over the soft intermediate layer 38.

Any decreased absorption resulting from saturation may be compensated for by using a passive dye on the inner or back surface of the lens. An effective dye for this purpose is quinizirin. The polarizing sheet for lenses is preferably incorporated over the front or outside surface of the lenses.

Solvent evaporated polymer coatings on polymer substrates are known. These coatings can also be the host for a photochromic metal dithizonate as described above.

The method of immersing the lenses is useful for plastic molded lenses as well as for lenses which are injection molded, or formed in other ways.

EXAMPLE 9

Following the procedure of Example 4, a lens suitable in a ski goggle is produced by imbibing (diphenyl thiocarbazono) phenylmercury (II) into a lens of polycarbonate sold under the trademark "Lexan" by immersing said lens in a solution of the above dithizonate heated to a temperature of 80° C for a period of about 10 minutes. The solvent utilized consists of propylene glycol. A photochromic lens is produced which after lamination with a polarizing sheet is suitable for use in a ski goggle.

EXAMPLES 10-15

In accordance with the procedure of Example 9, a polycarbonate lens is rendered photochromic by immersing said lens in a dye solution comprising (diphenylthiocarbazono) phenylmercury (II) heated to a temperature of 50° C for a period of 10 minutes. The following solvents are useful for dissolving the dye: equal proportions of ethanol and ethylene glycol (Example 10), propanol and 1,3-butylene glycol in equal proportions (Example 11), neopentyl glycol and butanol in equal proportions (Example 12), ethanol (Example 13), glycerol (Example 14), and the monomethyl ether of glycerol (Example 15). A photochromic lens suitable for use in a ski goggle is thus produced.

EXAMPLE 16

A photochromic lens is produced by the procedure of imbibing only the concave side of a concavo-convex lens of a polymer of diethylene diglycol bis allyl carbonate with quinizarin, a passive dye, and (diphenylthiocarbazono) phenylmercury (II) both present as saturated solutions in a mixture of toluene and ethylene glycol in accordance with the procedure of Example 2. The convex side of the lens is imbibed with a saturated solution of the same mercury dithizonate in a mixture of toluene and ethylene glycol. A suitable mechanical fixture in the form of a metal ring capable of holding two lenses and forming a solvent-impermeable seal where the ring contacts the lens is used to keep one side of the lens out of contact with the solvent during imbibition of the opposite side of the lens. A photochromic lens suitable for use in a ski goggle is thus produced.

EXAMPLE 17

Following the procedure of Example 2, a lens suitable as a ski goggle lens is produced by an imbibition process consisting of immersing a lens of a polymer of diethylene diglycol bis allyl carbonate in a solution of (diphenylthiocarbazono) phenylmercury (II) heated to a temperature of 80° C for a period of about 24 hours. The solvent which is used consists of a mixture of xylene and ethylene glycol in equal proportions. A suitable photochromic lens is produced in which the optical clarity of the lens is unaffected by the imbibition process.

While there have been shown and described what are considered to be preferred embodiments of the present invention, it will be obvious to those skilled in the art that various additional changes and modifications may be made in the invention, for example, the ski goggle lens materials and the methods for their formation may be utilized for photochromic filters, sunglasses, or other optical elements, without departing from the invention.

I claim:

1. Ski goggles and the like comprised of frame means defining apertures arranged to support lens means, said frame means arranged to be positioned on the head of a wearer to hold said lens means in front of the eyes of such a wearer, there being lens means filling said aperture means and arranged to be looked through by the wearer, said lens means comprised of at least one lens of allyl diglycol carbonate imbibed with an effective quantity of a metal dithizonate; the metal dithizonate being imbibed in said allyl diglyciol carbonate by immersing in the form of a lens in a heated, saturated solution of the metal dithizonate in toluene for an extended period of time sufficient to substantially uniformly disperse the dye throughout the lens, the dyed lens so produced being resistant to dye removal in heated aqueous media.

2. The ski goggle of claim 1 in which the resulting lens is an optically clear and relatively hard synthetic plastic lens substrate of variable optical density imbibed with a solution of a metal dithizonate in quantity effective to provide reduced luminous transmission upon activation by visible light.

3. A photochromic lens means according to claim 2 wherein said lens means comprises said synthetic polymer substrate and a polarizing layer.

4. The lens means of claim 3 wherein said polymer is selected from the group consisting of allyl polymers, polycarbonates, poly-lower aliphatic methacrylates, cellulosic polymers, vinyl polymers and hydroxylated polyethylene.

5. The lens means of claim 4 wherein said solution comprises a solvent selected from the group consisting of an aromatic hydrocarbon and mixtures thereof with (1) glycerol, (2) a glycol having 2 to about 8 carbon atoms and (3) an alcohol having 2 to about 10 carbon atoms.

6. The lens means of claim 5 wherein said passive dye is quinizarin.

7. The lens means of claim 5 wherein said polarizing layer comprises a polyvinyl alcohol or polyvinyl butyral layer and said solvent is a mixture of an aromatic hydrocarbon and a glycol having 2 to about 8 carbon atoms.

8. A lens means according to claim 5 wherein the metal dithizonate has the following general formula:

wherein M is selected from the group consisting of $Hg^{II}$, $In^{III}$, and $Ga^{III}$, when M is $Hg^{II}$ $x$ is equal to 1 or 2 and $y$ is equal to $2-x$ when M is $In^{III}$ or $Ga^{III}$ $x$ is equal to three and $y$ is equal to zero. R and R' are radicals individually selected from the group consisting of where $R^2$ is a radical selected from the group consisting of alkyl ($C_1$-$C_4$), nitro, halo, alkoxy, ($C_1$-$C_4$), aryloxy ($C_6$-$C_{10}$), hydroxy, carboxy, carboxyalkyl ($C_2$-$C_4$), alkoxycarbonyl ($C_2$-$C_6$), aryl ($C_6$-$C_{10}$), arylamino ($C_6$-$C_{10}$), acylamino ($C_1$-$C_{11}$), and alkylthio ($C_1$-$C_4$), and R" is a radical selected from a group consisting of alkyl ($C_1$-$C_{12}$), aryl ($C_6$-$C_{18}$), alkaryl ($C_7$-$C_{10}$), aralkyl ($C_7$-$C_{15}$), alkoxyalkyl ($C_2$-$C_{12}$), and aminoaryl ($C_6$-$C_{12}$).

9. A lens means according to claim 8 wherein R and R' are each phenyl rings.

10. A lens means according to claim 8 wherein R" is selected from the group consisting of phenyl, naphthyl, tolyl, ethyl, ethoxyethyl, benzyl, and p-aminophenyl.

11. A lens means according to claim 8 wherein the metal dithizonate is selected from the group consisting of bis (diphenylthiocarbazono) mercury (II), (diphenylthiocarbazono) phenylmercury (II), (diphenylthiocarbazono) p-tolylmercury (II), (diphenylthiocarbazono) β-naphthylmercury (II), (diphenylthiocarbazono) ethylmercury (II), (diphenylthiocarbazono) ethoxyethylmercury (II), (diphenylthiocarbazono) benzylmercury (II), (diphenylthiocarbazono) p-aminophenylmercury (II), tris (diphenylthiocarbazono)indium (III), and tris (diphenylthiocarbazono) gallium (III).

12. A lens means according to claim 8 wherein the metal dithizonate is bis (diphenylthiocarbazono) mercury (II) and wherein said substrate is a polymer of diethylene glycol bis allyl carbonate.

13. A lens means according to claim 8 wherein the metal dithizonate is (diphenylthiocarbazono) phenylmercury (II) wherein said substrate is a polymer of diethylene glycol bis allyl carbonate.

14. A lens means according to claim 8 wherein the metal dithizonate is (diphenylthiocarbazono) benzylmercury (II), wherein said substrate is a polymer of allyl diglycol carbonate.

15. A lens means according to claim 8 wherein the metal dithizonate is (diphenylthiocarbazono) p-aminophenylmercury (II), wherein said substrate is a polymer of allyl diglycol carbonate.

16. A lens means according to claim 8 wherein the metal dithizonate is tris (diphenylthiocarbazono) indium (III), wherein said substrate is a polymer of allyl diglycol carbonate.

17. A lens means according to claim 8 wherein the metal dithizonate is tris (diphenylthiocarbazono) gallium (III), wherein said substrate is a polymer of allyl diglycol carbonate.

18. A lens means according to claim 8 wherein the metal dithizonate is (diphenylthiocarbazono) ethoxythylmercury (II), wherein said substrate is a polymer of allyl diglycol carbonate.

19. A photochromic ophthalmic quality lens according to claim 1 wherein said lens means comprises said synthetic polymer substrate and a passive dye.

* * * * *